United States Patent [19]
Davidson

[11] Patent Number: 5,163,323
[45] Date of Patent: Nov. 17, 1992

[54] ULTRASONIC DISTANCE MEASURING INSTRUMENT

[75] Inventor: Amber Davidson, Salt Lake City, Utah

[73] Assignee: Ezra C. Lundahl, Inc., Logan, Utah

[21] Appl. No.: 466,757

[22] Filed: Jan. 18, 1990

[51] Int. Cl.[5] .................. G01F 23/28; G01S 15/02
[52] U.S. Cl. .................. 73/290 V; 73/597; 364/560; 364/561
[58] Field of Search ............. 73/290 V, 597; 364/560, 364/561

[56] References Cited

U.S. PATENT DOCUMENTS

| | | | |
|---|---|---|---|
| 3,237,451 | 3/1966 | Haeff | 73/290 V |
| 4,000,650 | 1/1977 | Snyder | 73/290 V |
| 4,221,004 | 9/1980 | Combs et al. | 73/290 V |
| 4,572,253 | 2/1986 | Farmer et al. | 73/293 |
| 4,665,924 | 5/1987 | Saito et al. | 73/631 |
| 4,733,355 | 3/1988 | Davidson et al. | 364/561 |

FOREIGN PATENT DOCUMENTS

8905442  6/1989  PCT Int'l Appl. .............. 73/290 V

*Primary Examiner*—Hezron E. Williams
*Assistant Examiner*—Rose M. Finley
*Attorney, Agent, or Firm*—M. Reid Russell

[57] ABSTRACT

A non-contact type ultrasonic distance measuring device that includes a micro processor for controlling operation of a transducer that functions as both a sonic transmitter and receiver. Micro processor programming provides a control scheme whereby an operator can program different modes of operation into the instrument by depressing buttons arranged on a rear display panel of the instrument. Mode programming is accomplished in a manner similar to setting a digital watch, with the modes displayed in a display window. The mode programming and component operation provide a gate scheme where gate control is provided through application of gain control through three (3) amplifiers, one of which is a fourth order bandpass filter that is operated by the micro processor to provide a controlled increase in gain or "Q" as the elapsed time from a transmission becomes greater. The program self-adjusts during operation to sense the distances to close targets and to targets as far away as seventy (70) feet and can provide an accurate identification of a target through clutter as may exist in some instrument applications. Pulsing control is also provided for in the mode programming, whereby, after a single pulse is sent, the instrument will not send a next pulse until the expiration of a set time period.

2 Claims, 7 Drawing Sheets

ULTRASONIC DISTANCE MEASURING INSTRUMENT

BACKGROUND OF THE INVENTION

1. Field of the Invention

This invention relates to ultrasonic non-contact sensing devices for measuring distances from a source as a measure of the time it takes for a sound wave to bounce off an object whose distance is being measured and returned to the source.

2. Utilization

In a number of situations it is necessary that a distance measurement to an object be made without actually contacting the object. Such situation may further require that the object distance be constantly monitored. Such non-contact monitoring may be required to prevent damage to a distance measuring sensor or to prevent damage or disruption to the object or surface being measured or monitored. Also, the presence of a hazardous environment may preclude the use of direct contact sensing or distance measuring, such as in the monitoring of a liquid level in a vat of a corrosive or caustic solution. With non-contact sensing, as actual contact is not required and, the distance measuring sensor can be physically isolated from the object, precluding damage to the sensor or to the surface of the object being monitored. Additionally, as measurements are made from a distance, the sensor and measurement device may be conveniently located outside of hazardous environments thereby preserving the integrity, accuracy, and reliability of the measuring equipment.

3. Prior Art

Ultrasonic sensors and apparatus are well known and, like the present invention, a number provide a capability for remote distance measuring. Examples of some of such earlier devices are shown in patents to Austin, et al., U.S. Pat. No. 4,170,765; Massa, U.S. Pat. No. 4,210,969; Newman, U.S. Pat. No. 4,584,676; Farmer, et al., U.S. Pat. No. 4,572,253; Soltz, U.S. Pat. No. 4,518,997; Schurr, U.S. Pat. No. 4,101,865; Carlin, et al., U.S. Pat. No. 4,487,065; a Soviet Union Patent No. 0,563,320; and a patent to Combs, et al., U.S. Pat. No. 4,221,004. Which Combs patent also provides for a voltage level adjustment to an amplifier. Neither the Combs patent nor any of the above, however, provide an instrument with versatility and reliability of the present invention that provides a doubling to tripling in sensing range over other known ultrasonic instrument of the same size sensor and power range.

A prior patent application owned by the owner of the present invention, Ser. No. 07/187,986, now abandoned, sets out an earlier ultrasonic distance measuring device, that was made and sold, that the present invention improves upon. The above-cited prior art references and others were cited against allowance of which application Ser. No. 07/187,986.

SUMMARY OF THE INVENTION

It is a principal object of the present invention to provide a non-contact ultrasonic distance measuring instrument that has increased range sensitivity over earlier ultrasonic distance measuring devices.

Another object of the present invention is to provide an ultrasonic distance measuring instrument with improved filtering capabilities to enable the device to pick up and discriminate weak signals.

Another object of the present invention is to provide an ultrasonic distance measuring instrument that is fully programmable and includes a programmable gain for improving sensitivity and excluding unwanted targets.

Still another object of the present invention is to provide an ultrasonic distance measuring instrument that is easily programmable at the unit.

Still another object of the present invention in an ultrasonic distance measuring instrument is to provide an instrument that can be used alone or as a master or slave unit in a gang of sensors.

Still another object of the present invention in an ultrasonic distance measuring instrument is to provide an instrument that does not require but can be used with a reference module where conditions require, and can be used with a wave guide.

The present invention is in an improved low power (under 50 ma when displays are turned off and under 100 ma with all displays on) ultrasonic distance measuring instrument. The present invention employs a linear integrated circuit sonic ranging module that drives an electrostatic or ceramic transducer that functions as both the sonic transmitter and receiver. The instrument of the present invention incorporates a very low noise amplifier and special filter techniques that allow it to pick up and discriminate signals that heretofore were too weak to be received and accurately interpreted. The instrument operates in a number of modes that are programmable through a push button interface on a panel arranged on the instrument rear face. Which push buttons are operated much like a digital watch.

The instrument includes a microprocessor programmed uniquely to synchronize pulses, preventing interference when the instrument is gauged, with like instruments, and to set the number of pulses transmitted as determined when the signal is on. The pulsing capability produces a narrow sound wave suitable for operation through a wave guide.

The microprocessor checks the distance to a target and boosts the instrument power level to a proper level and accordingly adjusts the programmable settings for the three (3) amplifiers. This gain increase can be programmed or automated as governed by the target distance, which is directly proportional to the time from the transmit pulse.

A third amplifier, of the three amplifiers, cited above, is further unique to the present invention in that it is a gain or "Q" adjustable band pass digital filter that heretofore has no been adjustable. The filter is preferably a switched capacitance digital filter. Gain or "Q" adjustment is increased by the system microprocessor as the elapsed time from a transmission becomes greater, automatically compensated for greater range. As the gain or "Q" climbs the band width becomes more narrow and accordingly any signal whose frequency varies from the center frequency is attenuated. The filter thereby acts as both an amplifier and filter, making possible a receipt and processing of a weak return signal for detection. Such signal would otherwise require noise amplification to intolerable levels. To provide this gain the system microprocessor rapidly changes filter gain or "Q" over a very short period of time, typically forty (40) times over a twenty (20) millisecond period.

Additionally, the instrument provides for system calibration against a reference module of compensation for conditions such as humidity and temperature as would alter the speed of sound. A first in first out (FIFO) memory is provided for averaging data as needed, for use as a reference against new data coming in. Which functions are simply programmed into and may be easily changed by operation of the control buttons on the instrument rear end that also includes a readout. So arranged, the instrument is very light and easily managed, is easily set up and programmed at the site and its program can be easily changed to compensate for actual conditions.

DESCRIPTION OF THE DRAWINGS

In the drawings that illustrate that which is presently regarded as the best mode for carrying out the invention.

DETAILED DESCRIPTION

Figure 2:
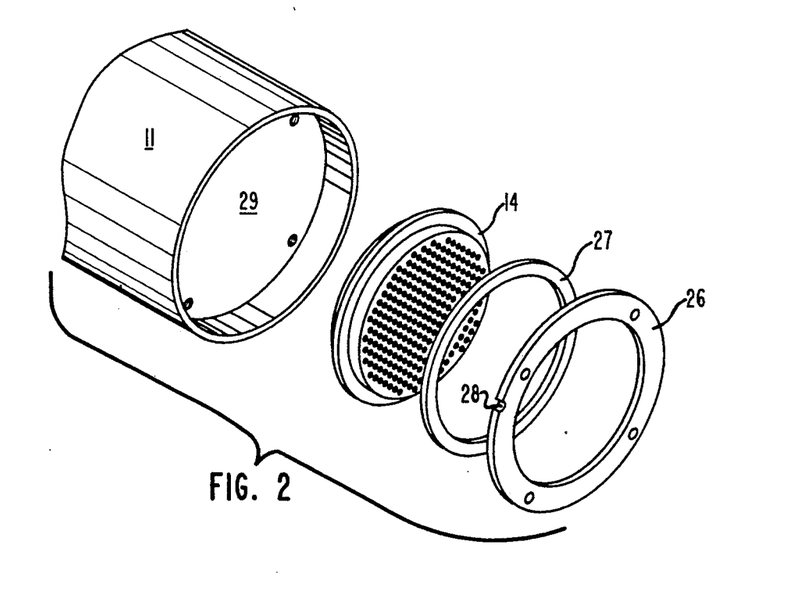
FIG. 2 is a partial perspective exploded view of the front end of the instrument of FIG. 1.
Figure 3:
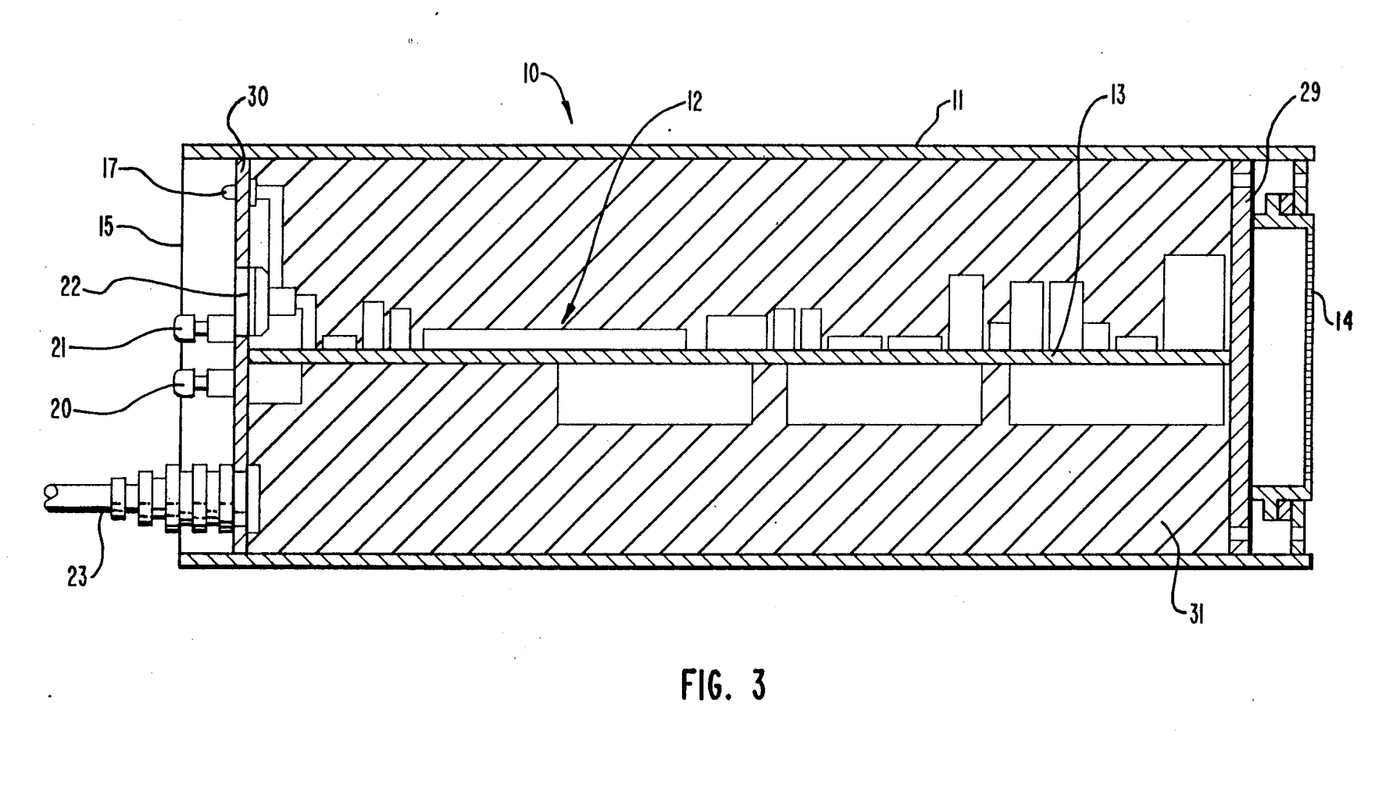
FIG. 3 is a vertical sectional view taken axially along the line 3—3 of FIG. 1.

An improved ultrasonic distance measuring instrument 10 of the present invention, hereinafter referred to as instrument, is shown generally in FIGS. 1 through 3. FIG. 3 shows best electrical components or electronics 12 of the instrument mounted on a board 13 and contained within a stainless steel cylindrical housing 11. The board may, but need not be, encapsulated within housing 11 by a potting solution as is well known. The cylindrical housing 11 seats, within and across its forward end, an electrostatic transducer 14. A rear end of which cylindrical housing is capped by a control and display panel 15.

Figure 1:
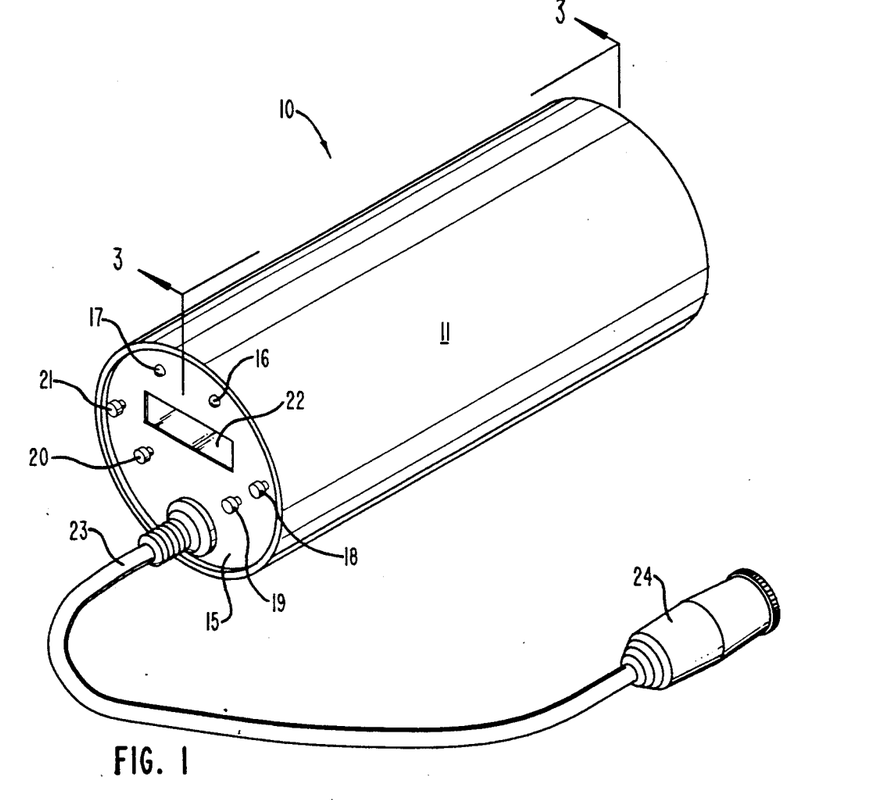
FIG. 1 is a perspective view of the improved distance measuring instrument of the present invention, showing the rear end panel with push buttons and a display window.

Shown on the display panel in FIG. 1 are two LED's, 16 and 17, labeled Gate 1 and Gate 2, respectively, whose function will be set out hereinbelow. Also, four (4) buttons are shown extending outwardly from the panel face. The buttons, clockwise from a mode button 18 on the panel right side, are down button 19; up button 20; and enter button 21. These buttons are spring biased outwardly and are connected to a microprocessor within the housing to provide, when depressed, programming information thereto, as will be set out in greater detail hereinbelow with reference to system functioning. The operation of which buttons is much like the process of setting a digital watch, with a readout LED (Light Emitting Diode) display 22 provided on the display panel 15 wherein programming inputted at the buttons is displayed.

Shown in FIGS. 1 and 3, the instrument 10 includes a control cable 23 that terminates in a multi-pin end connector 24. The control cable connects to flow paths on the board 13 whereon the electronics 12 are mounted. Shown in FIG. 2, the electrostatic transducer is exploded from the front of the cylindrical housing 11. The transducer 14 includes a case transducer seat, which is preferably a circular piece of fiberglass printed circuit board material. The electrostatic transducer 14 positioned within the housing 11, is held by a transducer retaining ring 26 that sandwiches a transistor O-ring 27 against the electrostatic transducer 14. The transistor O-ring 27 serves as a shock mount to prevent mechanical impact or mechanical vibrations from being detected as return sonic echoes. The transducer retaining ring 26 preferably includes a notch or hole 28 that serves as an air pressure relief or equalization port to equalize pressure on the back side of the electrostatic transducer 14, for preventing air pressure dampening of the transducer diaphragm.

FIG. 3 is a vertical longitudinal sectional view taken through the lines 3—3 of FIG. 1. As shown, the printed circuit board 13, bifurcates the cylindrical housing and extends between front and rear plates 29 and 30, respectively. With the printed circuit board 13 in position, a potting solution 31 may be poured thereon for both encapsulating the electrical components 12 and to provide damping of any vibration or jarring to which the electrical components would otherwise be subjected to. The potting, however, is optional and may be dispensed with, within the scope of this disclosure.

Figure 4:
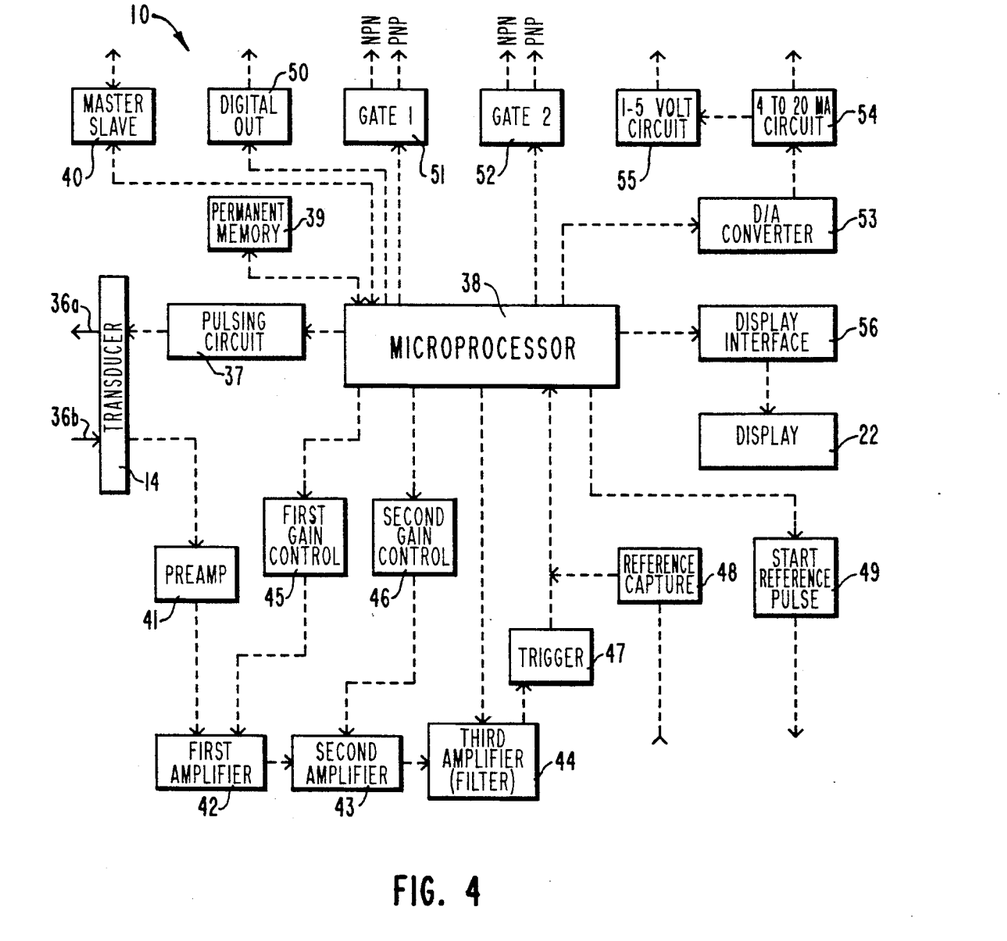
FIG. 4 is a block flow of the electronic components of the instrument.

FIG. 4 shows a block flow schematic of the electrical components of instrument 10. Instrument 10 is, of course, a distance measuring device that operates utilizing sound, calculating distance to a target based on the time it takes a sound wave to travel through the atmosphere. In operation, the transducer 14, described hereinabove with respect to FIG. 1, sends out a sound wave, arrow 36a, generated by a pulsing circuit 37, that hits a target and is reflected back, arrow 36b, and is detected. Heretofore, sonic distance measuring low power instruments have been generally limited to short ranges (usually thirty-two (32) feet or less) due to beam spread and energy losses that are experienced as the sound wave travels out and returns. With the present instrument 10 there is a very low noise amplifier and with special filtering techniques, as set out in detail hereinbelow, the instrument 10 can pick up weaker signals. Utilizing instrument 10 at low power, targets as far as one hundred (100) feet and as close as 20 hundreths (0.20) feet have been detected with the instrument drawing less than one hundred (100) ma of current. Instrument 10 does not utilize potentiometers (variable resisters) in its circuits, and provides that all of its adjustments are controlled through push buttons 18 through 21 on the display panel 15 of FIG. 1. Which push buttons are operated much like a digital watch, the time the individual button is depressed determining the mode the display is scrolled to. There are twenty-nine (29) modes or settings that can be programmed into the instrument 10, all of which are retained in the microprocessor 38 when power is turned off. In practice, a microprocessor known as a MC68HC705C8P, manufactured by Motorola, has been used successfully for this application. Explanation of the different modes is set out in detail hereinbelow.

In the operation of instrument 10, initializing system parameters and peripheral chips is performed when power is first applied. If a permanent memory 39 is empty, which memory is preferably a NMC 93C46N manufactured by National, a default table for the mode values is loaded into permanent memory 39 and into a RAM contained in the microprocessor 38. The permanent memory 39 will retain information without power, whereas the RAM does not retain information without power. Any mode information previously entered will also be loaded into RAM. Initializing the system is done only upon powering up the system.

Before a transmit pulse is sent, by pulsing circuit 37, a coded signal is transmitted. If the unit is a master, that signal is transmitted by a master slave block 40, to another instrument or instruments 10, that are set up as slaves. This signal tells other such units that it is time to transmit. This action is to synchronize the sound waves going out from the individual instruments to prevent interference between the units. When it is time to transmit, the microprocessor 38 first sends a signal to the pulsing circuit 37. The number of pulses that will be sent is determined by the time the signal is on. For example, one pulse per transmission results in a narrow sound wave that is suitable for use in a wave guide, as illustrated in FIG. 6(D).

Shown in FIG. 4, the microprocessor 38 then waits for the pulse blanking to end before checking for a return signal. A preamp 41 is connected to transducer 35 to boost the power level of the return signal to the proper level to a first amplifier 42. First and second amplifiers, 42 and 43, respectively, and a third amplifier 44 that is also a filter, all begin with a gain of one at the start of a transmission receive cycle. As time progresses before a return signal is received, the microprocessor 38 turns on first and second gain control circuits 45 and 46, respectively, which increase the gain of each amplifier 42 and 43, respectively. In practice, amplifiers known as OP27, manufactured by Motorola, have been used successfully for this application. All the gain controls are programmable. This process is also described as with respect to a discussion of modes set out hereinbelow. So arranged, the instrument 10 is very versatile for setting up gain curves in difficult situations. The gain can be lowered or blanked at distances where unwanted targets are found.

The third amplifier 44, that is a fourth order bandpass digital filter, is unique to the instrument in that the microprocessor is programmed to increase the gain or "Q" of this filter as elapsed time from transmission becomes greater. This functional capability has heretofore been unknown. In practice, a filter known as a MAX262, manufactured by Maxim, has been used successfully for this application. As the gain or "Q" climbs the bandpass will become more narrow, in that, as any signal whose frequency varies from a center frequency is attenuated. Signal attenuation will increase as the variation becomes larger with an increase in gain or "Q". Accordingly, third amplifier 44 acts as both a filter and an amplifier. In practice, utilizing a capacitance digital filer it was found that weaker return signals could be detected without amplifying the noise to intolerable levels. In fact, a target located approximately one hundred (100) feet from the sensor head was detected with this low power unit. In earlier regular analog amplifiers the noise produced at such distances would overpower the signal levels if the same overall gain were used. Rather than an analog amplifier, the instrument utilizes digital signals. The preferred third amplifier filter 44 is a switched capacitance digital filter, the gain or "Q" of which is changed very rapidly according to the settings in modes 8 and 9, as will be discussed hereinbelow. Typically the gain or "Q" can be changed forty (40) times over a twenty (20) millisecond period.

A trigger 47 is activated by the third amplifier 44 when a return signal is detected. The trigger in turn causes a hardware capture of the return time, shown at box 48, within a resolution of two microseconds. Calculations are performed in the microprocessor 38 on the captured time for calibration, offset and to convert time to distance. Additional calibration is done on the new distance if an optional reference calibration module, not shown, is attached to the unit. Such reference module is shown in the earlier cited "Distance Measuring Apparatus", Ser. No. 07/187,986 application, now abandoned, and compensates for conditions such as humidity and temperature that affect the speed of sound.

If the distance on the object is within limits set by mode 24, that will be discussed later herein, (out of range span) the data is placed in a (FIFO) first memory of the microprocessor 38 to be averaged in with past data. The number of samples averaged is a function of mode 22 that covers the number of samples to be averaged, shown also as a box labeled microprocessor 38. If the data is not within the proper limits and this occurs in succession for the number of times, as set by mode 23, then the FILO memory is filled with the new distance. This new distance or the calculated average then becomes the standard against which new data coming in is judged.

Figure 5:
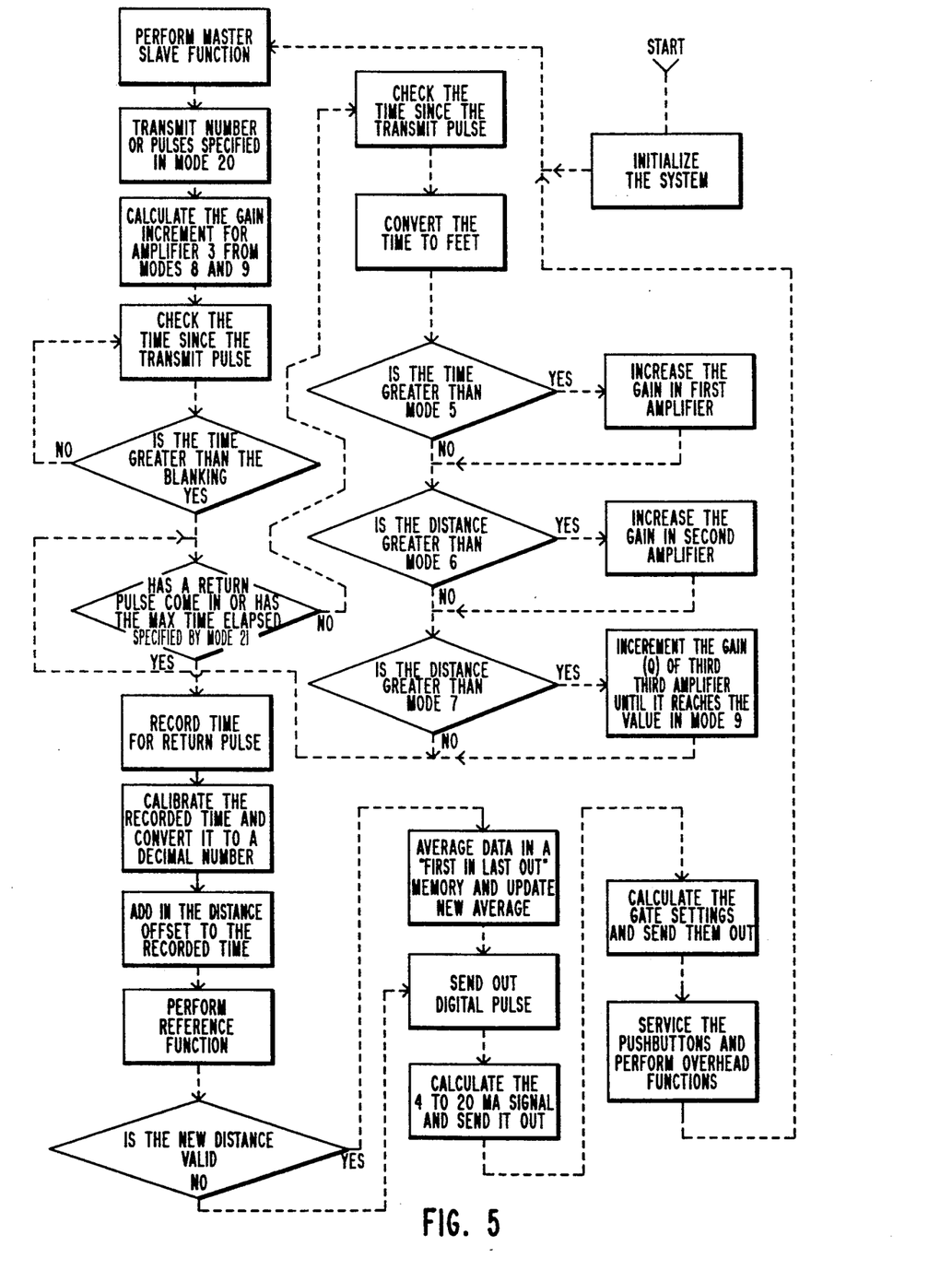
FIG. 5 is a logic flow chart of the operation and logic of the instrument.

The microprocessor 38 next makes a series of calculations as shown in the logic flowchart of FIG. 5. Signals are sent based on the average discussed above out a digital out 50, gates 51 and 52, and to four (4) to twenty (20) ma and one (1) to five (5) volt circuit boxes, 54 and 55, respectively, from a digital to analog converter 53 that is preferably a DAC 8043 manufactured by PMI. These signals are all based on programmable settings which are extremely easy to set up, as discussed hereinbelow relative to modes of operation of the instrument. The gates 51 and 52, respectively, have programmable modes that can be used to setup the instrument for an endless variety of applications. Which settings, from the microprocessor 38 pass through a display interface 56 to display 22 on the display panel 15 shown also in FIG. 1.

The last function performed by the microprocessor is a self check, utilizing the push buttons, to check the display and for some memory checking. The push buttons 18 through 22 allow the instrument settings to be changed as well as changing the display 22 that shows information about the modes and the average distance the unit is seeing. The microprocessor 38 then resets and starts over.

Certain components have been hereinabove identified with part numbers and by manufacturers. These components are preferred though it should be understood that other components of comparable characteristics could be employed within the scope of this disclosure and that the parts not identified are readily available components and accordingly specific components have not been identified herein.

FIG. 5 shows the instrument 10 logic flow as discussed above with respect to FIG. 4, and with respect to the program modes discussed below.

Hereinbelow is set out a mode table identifying the function of each of the twenty-nine (29) mode functions:

| MODE TABLE | |
| --- | --- |
| Mode No. | Value |
| 1 | Distance calibration (display in feet) |
| 2 | Distance offset (display in feet) |
| 3 | Offset Polarity (0-Positive, 1-Negative) |

MODE TABLE -continued

| Mode No. | Value |
|---|---|
| 4 | Blanking (display in feet) |
| 5 | Gain 1 (display in feet for amplifier stage 1) |
| 6 | Gain 2 (display in feet for amplifier state 2) |
| 7 | Gain 3 (display in feet filter) |
| 8 | Gain 3 span (display in feet for filter) |
| 9 | Gain 3 sensitivity (0–128) |
| 10 | 4 ma distance (display in feet) |
| 11 | 20 ma distance (display in feet) |
| 12 | 4 ma calibration (0–4095) |
| 13 | 20 ma calibration (0–4095) |
| 14 | Begin gate 1 (display in feet) |
| 15 | End gate 1 (display in feet) |
| 16 | Gate 1 modes (0–5) |
| 17 | Begin gate 2 (display in feet) |
| 18 | End gate 2 (display in feet) |
| 19 | Gate 2 modes (0–5) |
| 20 | Number of transmit pulses (0–50) |
| 21 | Distance range (display in feet) |
| 22 | Number of samples to average (0–35) |
| 23 | Number of out of range samples (0–255) |
| 24 | Out of range span (display in feet) |
| 25 | Reference (0-no reference, 1 -reference) |
| 26 | Master/Slave (0-master, 1-slave) |
| 27 | Display (0-off, 1-on) |
| 28 | Reset (0–100) |
| 29 | Software version |

The mode table set out above lists all the mode numbers, titles, and what is displayed on the instrument display 22. By depressing the mode button 18 on the instrument display panel 15 the mode number is displayed. Continually pressing and releasing that mode button causes the mode number to cycle up or down, number by number. It is possible to change the cycle direction of the mode number. This is done by holding down on the mode button, momentarily pressing the up or down buttons 20 and 19, respectively, so as to increment or decrement the mode number. After releasing either the up or down button the mode number will continue to cycle in the proper direction until the mode button is released. The mode button is released at the desired mode. The up or down button is depressed to display the current mode value. To change the current mode value, the up or down button is pressed and held until the right value scrolls into place. The enter button 21 can then be depressed to permanently store the displayed value. The value entered will be retained even when the instrument loses power. If the enter button 21 is not pushed the value will be stored in RAM only and lost when power is turned off. Whenever the enter button 21 is pressed the instrument displays the current distance. To display the current distance without permanently storing the results, change the mode value with the up or down button, press the mode switch, and then push the enter button.

Mode 1. Distance Calibration

Temperature, humidity, and other environmental conditions such as the type of gas affect the speed of sound. Mode 1 is provided to bring the distance reading in line with the actual distance. This is accomplished by multiplying the measured time to a target by a calibration factor. This factor can be changed by the up or down buttons when in mode 1. The display reads in feet the distance the instrument is seeing after multiplying by the calibration factor. When the up switch is pressed and held the distance will increase on the display. The opposite occurs for the down switch. The digital out signal also reflects what calibration factor is used. Alternatively, a feedback monitor, not shown, extending a fixed distance from the sensor end can be employed as a reference point for determining such calibration factor.

Mode 2 and 3. Distance Offset and Offset Polarity

The distance in mode 2 is added or subtracted on to the calibrated distance according to the setting in mode 3. A "0" in mode 3 is interpreted as a positive distance or an addition. A "1" in mode 3 is taken as a negative distance. For example if zero (0) feet were to start at three (3) feet from the transducer head, (normally zero (0) feet) you would go to mode 2 and across in a three (3) foot reading in the display with the up or down switches In mode 3 you would enter in a "1" for a negative distance. Any target from the end of the sensor to less than three (3) feet would now be displayed as zero (0) feet. A target at three (3) feet would read zero (0) feet and a target at ten (10) feet would read as seven (7) feet. A distance entered in for the gates or four (4) to twenty (20) ma, 51, 52 and 54, respectively, will have to take into account this offset. The digital out signal also reflects what offset factor is used.

Mode 4. Blanking Distance

The distance from the head of the instrument to a specified point that the instrument cannot read or ignores is known as the blanking distance. Ringing in the transducer head makes it necessary to always have some blanking after sending the transmit pulse. An electrostatic transducer 14 has less ringing than a ceramic transducer and the blanking distance can be as low as point twenty-five (0.25) feet when pulsed only once. Ceramic transducers usually must be blanked at least one (1) foot or more. A utilization of wave guides require that blanking be extended beyond the end of the wave guide structure. If the blanking is too small for a given situation the instrument 10 will always read a distance that is close to what the blanking is, regardless of any targets near by.

Modes 5, 6, 7, 8 and 9. Gain Adjustments

The instrument 10 has a versatile gain capability, allowing it to be utilized in many difficult situations involving sound applications. As sound travels and spreads out the return signal becomes weaker with distance. Accordingly, the system gain must increase with distance or time to detect the returning signal. Problems can, of course, arise if the gain is too great at the particular distance in that high gain has the effect of creating a wider field of view, particularly at close distances. Unwanted targets such as defects in a floor or wall, may therefore be picked up. For this reason the gain must be configured for each particular application.

There are three variable amplifiers 41, 42 and 43, respectively, in the instrument 10. Each amplifier starts out with a gain of 1. Where each amplifier begins to increase in gain is determined by modes 4, 6 and 7. All three modes display in feet the starting distance where the increase in gain begins. Mode 4 or gain 1 for first amplifier rises slower than the gain 2 of second amplifier. Gain 3 or the third amplifier, that is a filter, is the most versatile as it is completely adjustable. Gain 3 specifies where the increase in gain starts. Gain 3 span (mode 8) determines for how many feet the increase will continue. Mode 8 has a span of gain 3 for the gain rise and Mode 9 has a maximum "Q" and gain of gain 3.

Gain 3 sensitivity is the highest gain level the amplifier will rise too. Sensitivity can be as high as one hundred twenty-eight (128) however such level normally is not recommended due to a potential for amplifier unstability at that level. Normal operation would usually not exceed one hundred ten (110). At a "Q" of 110, the gain would be approximately 25 times and the filter ban pass would be very narrow. A sensitivity or Q of seventy-two (72) will have a gain of approximately only 2 times with a broad ban pass. This increase in "Q" is exponential so that at the higher number such as one hundred (100) or above, the increase in gain is dramatic with each increment. These five (5) adjustments afford instrument 10 with incredible flexibility in its many and varied applications. The following four (4) examples are set out to describe gain adjustments.

Figure 6A:
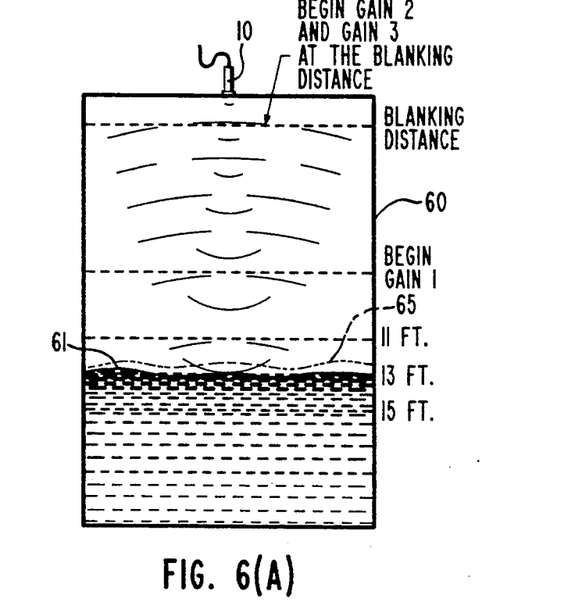
FIG. 6(A)-6(D) show plan views of the instrument of the present invention utilized in different configurations for measuring tank liquid levels.

A First Example—Refers to FIG. 6(A)

Shown therein, instrument 10 is mounted to the center of the top of a tank 60 looking down on a target such as a liquid level 61. In high humidity or a harsh environment a ceramic transducer should be used in lieu of the electrostatic transducer 14. The instrument 10 is shown positioned in the center of the tank 60, away from any walls or objects that it could prematurely pick up if the gain was too high. For this reason all three (3) amplifiers can begin to increase in gain at short distances. The gain for the second and third amplifiers is set to begin to rise at a blanking distance of two (2) feet. The first amplifier remains at a gain of 1 until it reaches eight (8) feet where it then begins to rise. This lowers the gain in the beginning as a function of distance compared with the situation where gain 1 starts at the blanking distance. It should be pointed out that at longer distances the overall gain will rise to the same maximum value regardless whether gain 1 is set to start at eight (8) feet or at the blanking distance. Gain 1 always rises to its maximum gain in a fixed amount of time. Overall maximum gain can be limited or raised by adjusting the sensitivity for gain 3. Gain 2 starts at the blanking distance because the rise time for this amplifier is faster than gain 1. Higher gain in the beginning is not a problem in this application. Maximum distance in the tank is only twenty (20) feet so the gain on gain 3 need only be set to eighteen (18) feet and the sensitivity set to one hundred (100). This application is easy to set up and there are many starting distances for the gains and values of sensitivity and span for gain 3 that would work.

Figure 6B:
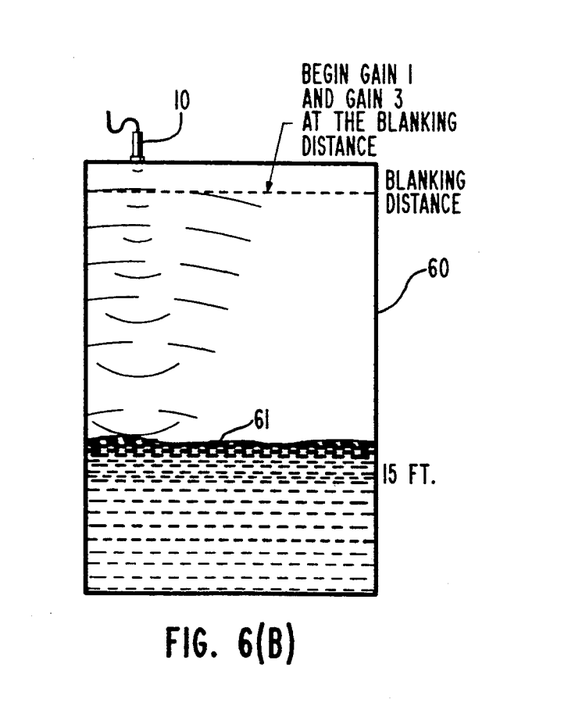

A Second Example relates to FIG. 6(B)

Herein the instrument 10 is shown located close to the tank 60 wall. The wall could have defects or corrosion that would reflect sound and be picked up as a legitimate target if the gain at that distance were sufficiently high. With trial and error it is determined that bringing gain 2 down to fifteen (15) feet will eliminate the problem and the sensor will not pick up the wall. Gain 1 is now chosen to start at the blanking distance because it has a slower rise in gain compared to gain 2. It should be pointed out that this arrangement will work with many configurations. So arranged, the target or liquid level 61 will give a large return signal as compared to anything else allowing the gain to be lowered. For example gain 3 could be chosen to start at some value past the blanking distance or the overall gain could be lowered by lowering the sensitivity for gain 3.

However, generally, at lower temperatures sound travels with less loss in an atmosphere of gas. This has the effect of making the gain appear greater. Accordingly, it should be verified that an initial gain curve is low enough in applications where the sensor could pick up unwanted targets with lower temperatures or an increase in gain.

One way of lowering the gain without adjusting the gain modes, is by limiting the number of pulses the transducer sends out (see mode 20) discussed hereinbelow. This also has the added feature of creating a narrower sound pulse to minimize the effect of the sound spreading out.

Figure 6C:
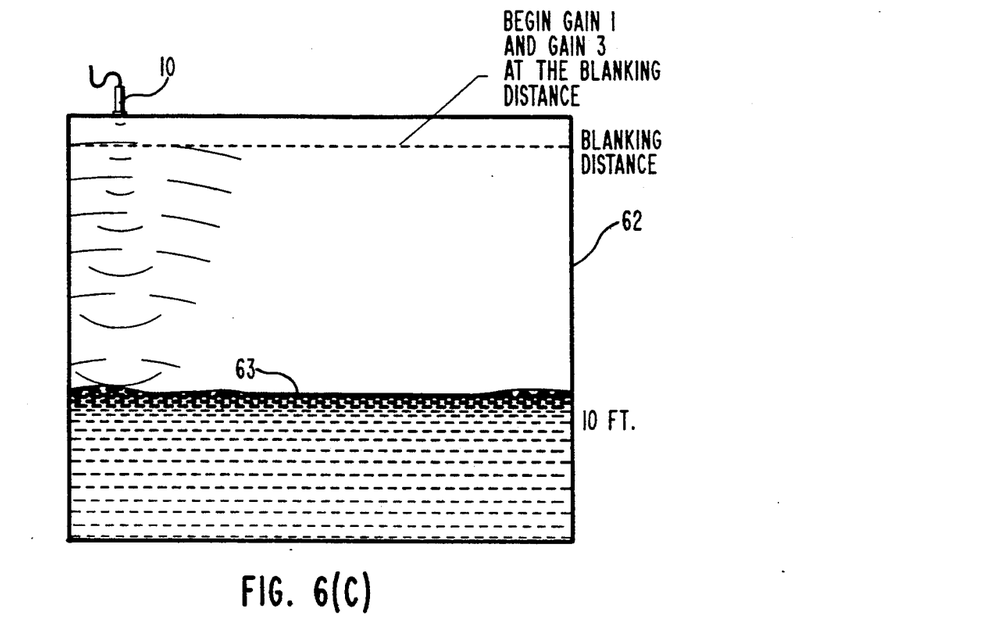
Figure 6D:
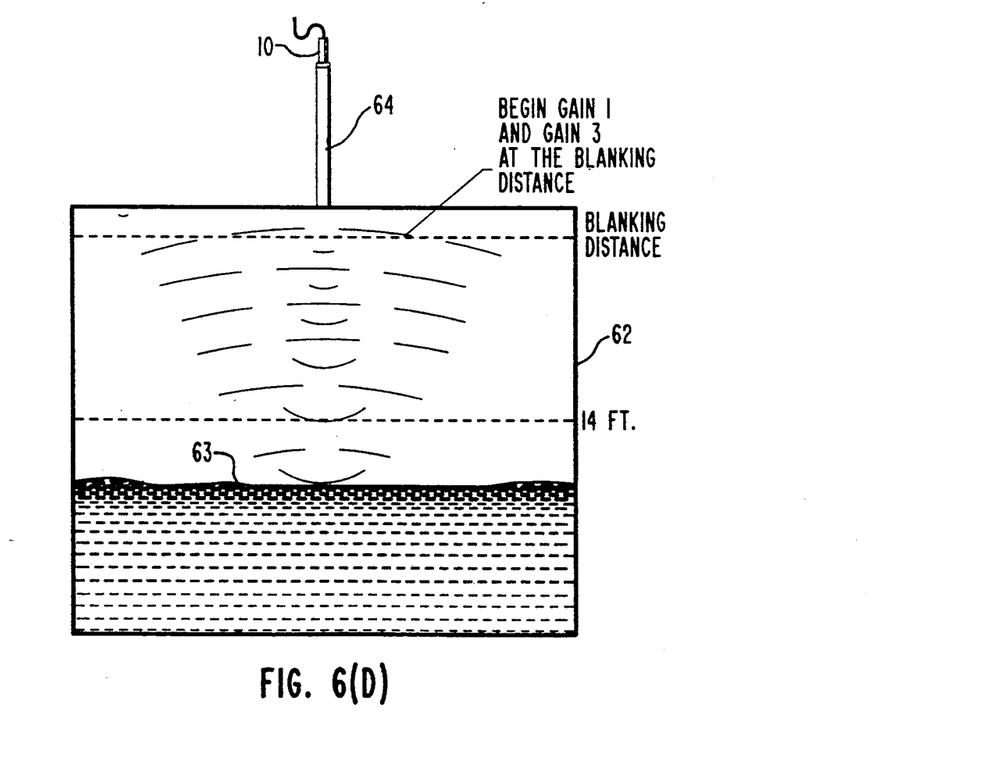

A Third Example Refers to FIG. 6(C)

This arrangement involves a smaller tank 62 with the instrument 10 positioned close to the tank 62 wall. With only ten (10) feet to look at the second amplifier 43 is not needed. Accordingly, by placing gain 2 beyond the end of the tank it essentially eliminates any effect it would have on the application. Sensitivity is also set at eighty (80) due to the short distance.

A Fourth Example Refers to FIG. 6(D)

A wave guide 64 is used in this configuration that can create problems due to reflections or vibrations within the narrow wave guide tube. Also, a change in medium from the wave guide into the tank may cause a reflection that can extend past the blanking distance. This condition is created due to vibrations inside the wave guide that use up time as the signal bounces back and forth making the distance appear farther. In situations like this the gain should be kept lower than normal near the front end of the wave guide tube or a few feet beyond the blanking distance. Pulsing transducer 14 one time for each reading cuts down the reflections inside the wave guide.

The above four examples are included to illustrate the versatilely of instrument 10, that can be configured to work in practically any situation.

Modes 10, 11, 12, 13—14 to 20 MA (1 to 5 Volt) Adjustments

Figure 7A:
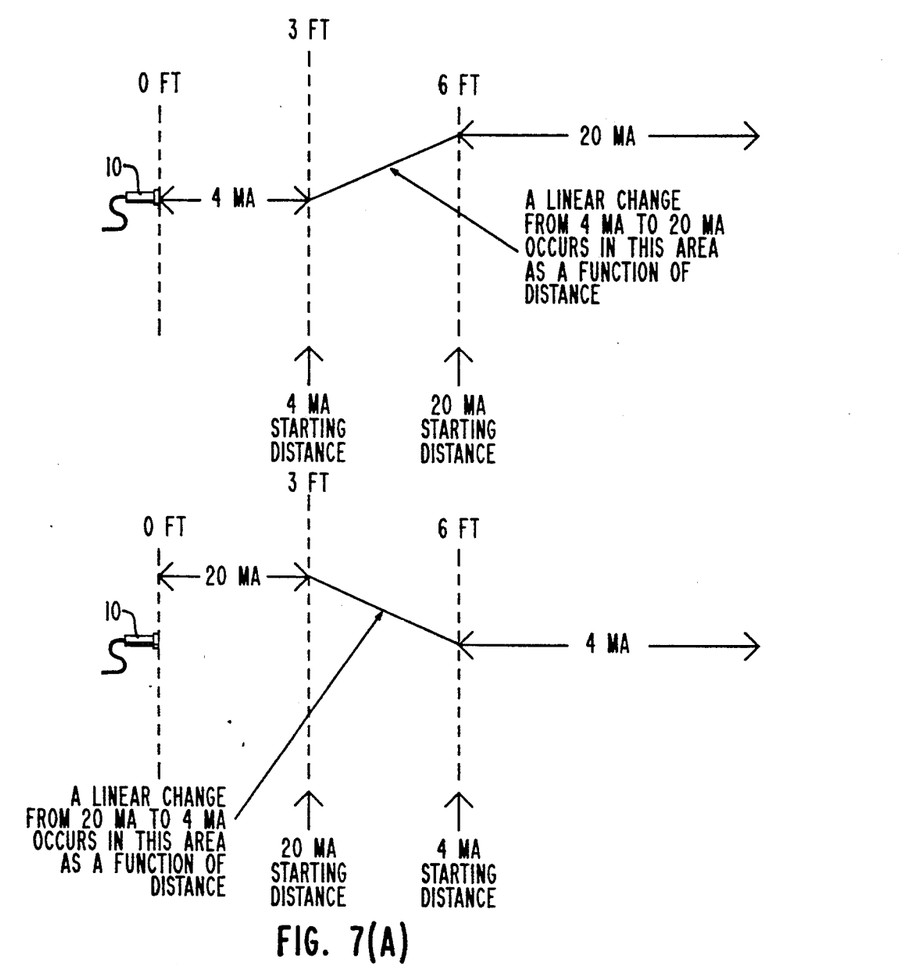
FIG. 7(A) and 7(B) show mechanical schemes illustrating how, through a feedback and adjustment, the instrument adjusts the gate distances form the sensor end to the distance being measured.

The current loop of these modes is very straightforward and easy to set up. Simply enter in the 4 ma distance in mode 10 and the twenty (20) ma distance in mode 11. 7(A) gives an example of how the current changes with distance. The change in current is linear with distance except on the outer edges where it remains constant. The two extreme reading may be off slightly and can be adjusted. This is done by connecting a current meter to the four (4) to twenty (20) ma line and pointing the transducer at a target that will get one of the extreme reading i.e. four (4) or twenty (20) ma reading into adjustment. The one (1) to five (5) volt option works with the same mode number. A pin on the back of the instrument must be shorted to ground and the four (4) to twenty (20) ma line disconnected to utilize this calibration option. The four (4) and twenty (20) ma distances (Modes 10 and 1) correspond to one (1) and five (5) volts respectively. The two (2) extreme voltage reading may be off slightly and can be adjusted. This is done by connecting a voltage meter to the one (1) and to five (5) volt lines and pointing the transducer at a target that will get one of the extreme readings i.e. one (1) and five (5) volts. The modes 12 and 13 are then scrolled to bring the one (1) or five (5) volt reading in exactly into adjustment.

Modes 14, 15, 16, 17, 18 and 19—Gate Adjustments

Figure 7B:
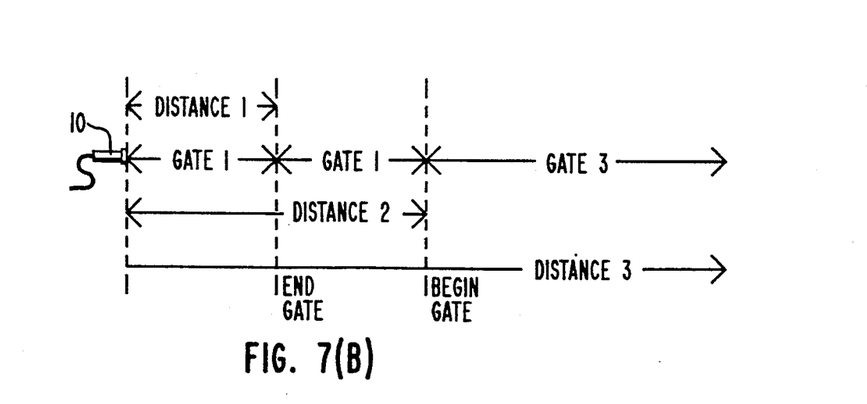

There are two (2) separate gates used to turn electronics, such as relays on and off. The gates can change up to 200 ma. Modes 14 and 15 control gate 1 and determine at what distance the gate turns on and off. Likewise modes 17 and 18 do the same for gate 2. Modes 16 and 19 determine what modes gate 1 and gate 2 are in respectively. With reference to FIG. 7(B), for example, to place gate 1 into mode 0, go to mode 16 (gate 1 modes) and enter in "0". Next enter a distance in mode 14 (gate 1 begin distance) where the transition from on to off is to occur. Then enter a distance in mode 15 (gate 1 end distance). The distance in mode 15 determines on which side of the mode 14 distance the gate turns on or off, shown at gates 1, 2 and 3. This provides a sensing distance 1, 2 or 2, wherein the target lies. Note, as set out above, the distance 3 can be as great as one hundred (100) feet for the low power instrument 10. However, in practice, instrument use is generally limited to a maximum distance of seventy (70) feet on the readout.

Gate width is controlled by simply entering in a distance in modes 14 or 15 and on modes 17, 18. The difference between the distances in the two respective modes is the gate width. How the instrument responds to the widths is determined by the mode setting in modes 16 or 19.

Mode 20. Number of Transmit Pluses

The instrument 10 operates by sending a transmission pulse out at a particular frequency and measuring the time it takes for a return echo. Mode 20 controls how many times the transducer 14 is pulsed or cycled for each return echo. Up to a certain distance form the transducer, the longer the transducer is pulsed, the stronger the return echo and the wider the sound wave is traveling out. This effect is more pronounced in ceramic than in electrostatic transducers. This feature is very useful in applications where a soft sound wave is needed such as in wave guides or where the out going wave is close to objects that should be ignored by the instrument. If only one pulse is transmitted and received, a "1" is entered into mode 20. Mode 20 allows up to fifty (50) pulses for each reading.

Mode 21—Distance Range

Mode 21 reads out in feet the maximum distance the instrument 10 looks at before sending another sonic burst. Smaller distances have the advantage of more readings with time. Caution should, however, be used when the maximum distance is made small enough that the sensor can pick up signals from a previous burst after sending a new sonic burst. This condition will cause errors in the readings. The maximum distance where this occurs is entirely dependent on the use the instrument is applied to. Where large solid targets such as flat hard walls or floors occur the chance of this happening is increased. In cases of large targets, maximum distances should be made large in relation to the distance of the first echo. Distances greater than forty (40) feet usually do not cause this problem.

Mode 22. Number of Samples to Average

Each distance reading can be averaged over time with previous readings. The more samples are averaged the steadier the output. FIG. 6(A) shows, at broken line 65, a turbulent liquid level in a tank. This varying liquid level would cause, without averaging, readings to be unstable. With averaging, the signal will reflect from the level as if it had no turbulence. Up to thirty-five (35) samples can be averaged in the F first memory. The number seen in the display in mode 22 is the number of samples which are averaged. By entering a "1" in mode 22, averaging is not provided for.

Modes 23 and 24. Out of Range Samples

In most applications the target has some maximum rate at which the target distance can change with time. Mode 24 (out of range span) sets up a span from the current distance such that any return signal falling outside this range will be ignored. FIG. 6(A) illustrates a situation where two (2) feet has been entered into Mode 24 with a current target distance of thirteen (13) feet. Accordingly, if a distance return above fifteen (15) or below eleven (11) feet is received it will be ignored unless this out of range signal is received in succession greater than the number of times specified in mode 23. This false signal could occur for a number of reasons such as someone pounding on the tank or high frequency sound generated form equipment. If the application were outside, a bird flying by could act as a temporary target. Whatever the reason modes 23 and 24 provide an option with enough versatility to fit most application. This feature can be disabled by entering a "1" in mode 23.

Mode 25. Reference

Temperature, humidity and other environmental conditions such as the type of gas affect the speed of sound. The instrument 10 has an optional reference module that can be attached thereto. The reference module, not shown, operates by sending a signal to a fixed target. Any changes in distance would be a result of the environment. The reference module accordingly sends this distance information back to the instrument which distance is used to compensate the distance measurement of the main target. Enter a "0" in mode 25 if no reference is required. A "1" inputted into mode 25 tells the instrument that a reference module is attached.

Mode 26. Master/Slave

Some applications require multiple instruments 10 which each send their own sonic burst. To avoid interference, the instrument 10 can be set up such that all instruments send the burst at the same time. To accomplish this, one of the instruments becomes a master and the rest are slaves. The master tells the slaves when to pulse. In a single instrument application that would be a master. The distance range (mode 21) for the master should be greater than the slaves for the slaves to transmit as often as possible. A "0" means master and a "1" in a slave in mode 26.

Mode 27. Display On/Off

The display 22 will turn off after approximately 10 minutes if no buttons are pressed when a "0" is entered for mode 27. Whenever any of the four (4) buttons are pressed the display will come on again, and remain on until ten (10) minutes after the last time a button was used. A "1" in mode 27 will keep the display on continually.

Mode 28. Reset

When the instrument 10 is powered up for the first time a default table is loaded for the modes. A seventy-seven (77) is loaded into modes 28 to direct the system not to keep loading in the default table each time power is turned on or off. Should the adjustment set into the system become scrambled, or for some reason it is desired to load the default settings, a number other than seventy-seven (77) is entered into mode 28. Thereafter turning the power on or off will cause all the modes to be loaded with the default parameters only upon the first power up.

Mode 29. Software Version

A software version is provided containing the approximate date of manufacture and operating version. This mode 29 when called up has no adjustment and is used for information only.

While a preferred embodiment of the present invention in an improved ultrasonic distance measuring instrument has been shown and described herein, it should be understood that the present disclosure is made by way of example only and that variations and changes thereto are possible without departing from the subject matter and reasonable equivalency thereof coming within the scope of the following claims, which claims I regard as my invention.

I claim:

1. An improved ultra-sonic distance measuring instrument comprising, a housing; a transducer on a forward end of said housing for sending and receiving sonic pulses; a display panel on a rear end of said housing; means for connecting said transducer to an electrical power source; microprocessor means connected to said transducer for controlling the transducer operation to determine a distance to a target from the time it takes a pulse sent by said transducer to be transmitted to and returned to said transducer from a target; means for programming said microprocessor means; and a pair of amplifiers and a filter connected to said microprocessor and said transducer, which said amplifiers are controlled by said microprocessor to establish variable gates by gain control for limiting said pulse reception, and said filter is operated as a fourth order band pass filter with said microprocessor changing the gain or Q of said filter approximately forty (40) times over approximately a twenty (20) millisecond period of time.

2. An improved ultrasonic distance measuring instrument as recited in claim 1, further including means controlled by said microprocessor for limiting transmissions from said transducer to a specific programmable time.

* * * * *